US011265650B2

(12) United States Patent
Xu et al.

(10) Patent No.: US 11,265,650 B2
(45) Date of Patent: Mar. 1, 2022

(54) METHOD, CLIENT, AND ELECTRONIC DEVICE FOR PROCESSING AUDIO SIGNALS

(71) Applicant: Alibaba Group Holding Limited, Grand Cayman (KY)

(72) Inventors: Yunfeng Xu, Hangzhou (CN); Tao Yu, Hangzhou (CN); Li Liu, Hangzhou (CN)

(73) Assignee: ALIBABA GROUP HOLDING LIMITED, Grand Cayman (KY)

( * ) Notice: Subject to any disclaimer, the term of this patent is extended or adjusted under 35 U.S.C. 154(b) by 370 days.

(21) Appl. No.: 16/452,771

(22) Filed: Jun. 26, 2019

(65) Prior Publication Data

US 2020/0015008 A1 Jan. 9, 2020

(51) Int. Cl.

| | |
|---|---|
| ***A61F 11/06*** | (2006.01) |
| ***H04R 3/04*** | (2006.01) |
| ***G10L 21/0232*** | (2013.01) |
| ***H04R 5/04*** | (2006.01) |
| ***H04R 3/00*** | (2006.01) |

(52) U.S. Cl.

CPC ............ *H04R 3/04* (2013.01); *G10L 21/0232* (2013.01); *H04R 3/005* (2013.01); *H04R 5/04* (2013.01)

(58) Field of Classification Search

CPC ...................................................... A61F 11/06

See application file for complete search history.

(56) References Cited

U.S. PATENT DOCUMENTS 2,986,608 A 5/1961 Pettus et al.
3,946,165 A * 3/1976 Cooper ............ G11B 20/00992 369/88
4,204,091 A * 5/1980 Ishigaki ............... H04B 1/1661 369/89
4,476,501 A 10/1984 Hirota et al.
5,402,500 A * 3/1995 Sims, Jr. ................ H03G 3/301 381/108
5,740,256 A * 4/1998 Castello Da Costa ...................... H04R 3/005 381/94.7
6,167,253 A 12/2000 Farris et al.
6,496,581 B1 * 12/2002 Finn ...................... H04M 9/082 379/406.01
7,404,001 B2 7/2008 Campbell et al.
8,204,884 B2 6/2012 Freedman et al.

(Continued)

*Primary Examiner* — Olisa Anwah

(74) *Attorney, Agent, or Firm* — James J. DeCarlo; Greenberg Traurig, LLP

(57) ABSTRACT

The disclosure describes methods, clients, and electronic devices for processing audio signals. One method for processing audio signals comprises: receiving a first audio signal inputted from a first audio acquisition terminal and a second audio signal inputted from a second audio acquisition terminal, wherein the first audio acquisition terminal and the second audio acquisition terminal are located in different positions of a same location; determining a target audio signal and a reference audio signal from the first audio signal and the second audio signal; determining a filter coefficient corresponding to the target audio signal based on the reference audio signal; and eliminating, from the target audio signal, a crosstalk signal determined based on the filter coefficient and the reference audio signal. The effect that a speech path can output speech signals with less interference is achieved.

20 Claims, 7 Drawing Sheets

(56) References Cited

U.S. PATENT DOCUMENTS

| | | | | |
|---|---|---|---|---|
| 8,606,249 | B1 * | 12/2013 | Goodwin | H04L 12/1827 455/416 |
| 9,179,236 | B2 | 11/2015 | Robinson et al. | |
| 9,332,126 | B2 | 5/2016 | Tadayon et al. | |
| 9,380,388 | B2 | 6/2016 | Bazarjani et al. | |
| 9,693,137 | B1 * | 6/2017 | Qureshi | H04R 27/00 |
| 9,996,315 | B2 | 6/2018 | Barnes, Jr. | |
| 10,044,409 | B2 | 8/2018 | Barzegar et al. | |
| 10,552,114 | B2 * | 2/2020 | Chakra | G06F 3/165 |
| 2005/0254440 | A1 | 11/2005 | Sorrell | |
| 2006/0008091 | A1 | 1/2006 | Kim et al. | |
| 2007/0291667 | A1 | 12/2007 | Huber et al. | |
| 2009/0041263 | A1 | 2/2009 | Hoshuyama | |
| 2012/0099733 | A1 | 4/2012 | Wang et al. | |
| 2015/0201278 | A1 * | 7/2015 | Bao | H04R 3/005 381/92 |
| 2016/0314778 | A1 * | 10/2016 | Christoph | G10K 11/17825 |
| 2016/0358107 | A1 * | 12/2016 | Kokkinis | G06N 20/00 |
| 2018/0158467 | A1 * | 6/2018 | Suzuki | H04R 3/02 |

* cited by examiner

METHOD, CLIENT, AND ELECTRONIC DEVICE FOR PROCESSING AUDIO SIGNALS

CROSS-REFERENCE TO RELATED APPLICATIONS

This application claims the benefit of priority of Chinese Application No. 201810718185.8, titled "A METHOD, CLIENT AND ELECTRONIC DEVICE FOR PROCESSING AUDIO SIGNALS," filed on Jul. 3, 2018, which is hereby incorporated by reference in its entirety.

BACKGROUND

Technical Field

The disclosed embodiments relate to the field of computer technologies, and in particular, to methods, clients, and electronic devices for processing audio signals.

Description of the Related Art

During in-person meetings, people communicate and discuss issues. In some of these meetings, microphones may be used to amplify one or more speakers. When there are multiple microphones operating in such a setting, audio signals from multiple persons or sources can be acquired and crosstalk may occur among different audio signals which negatively impacts the overall speech output of the system employing the microphones. The resulting output of such a system is thus at least partially degraded due to said crosstalk.

SUMMARY

The disclosed embodiments provide methods, clients, and electronic devices for processing audio signals which remedy the problem identified above by accurately eliminating crosstalk.

One embodiment provides a method for processing audio signals, comprising: receiving a first audio signal inputted from a first audio acquisition terminal and a second audio signal inputted from a second audio acquisition terminal, wherein the first audio acquisition terminal and the second audio acquisition terminal are located in different positions of a same location; determining a target audio signal and a reference audio signal from the first audio signal and the second audio signal; determining a filter coefficient corresponding to the target audio signal based on the reference audio signal; and eliminating, from the target audio signal, a crosstalk signal determined based on the filter coefficient and the reference audio signal.

Another embodiment provides a client, comprising: a first audio acquisition terminal, configured to input a first audio signal; a second audio acquisition terminal, configured to input a second audio signal, wherein the first audio acquisition terminal and the second audio acquisition terminal are located in different positions of a same location; and a processor, configured to determine a target audio signal and a reference audio signal from the first audio signal and the second audio signal; determine a filter coefficient corresponding to the target audio signal based on the reference audio signal; and eliminate, from the target audio signal, a crosstalk signal determined based on the filter coefficient and the reference audio signal.

Another embodiment provides a method for processing audio signals, comprising: receiving a first audio signal inputted from a first audio acquisition terminal and a second audio signal inputted from a second audio acquisition terminal, wherein the first audio acquisition terminal and the second audio acquisition terminal are located in different positions of a same location; determining a target audio signal and a reference audio signal from the first audio signal and the second audio signal; and sending the target audio signal and the reference audio signal to a server, so that the server determines a filter coefficient corresponding to the target audio signal based on the reference audio signal; and eliminates, from the target audio signal, a crosstalk signal determined based on the filter coefficient and the reference audio signal.

Another embodiment provides a client, comprising: a first audio acquisition terminal, configured to input a first audio signal; a second audio acquisition terminal, configured to input a second audio signal, wherein the first audio acquisition terminal and the second audio acquisition terminal are located in different positions of a same location; a processor, configured to determine a target audio signal and a reference audio signal from the first audio signal and the second audio signal; and a network communication unit, configured to send the target audio signal and the reference audio signal to a server, so that the server determines a filter coefficient corresponding to the target audio signal based on the reference audio signal; and eliminates, from the target audio signal, a crosstalk signal determined based on the filter coefficient and the reference audio signal.

Another embodiment provides a method for processing audio signals, comprising: receiving a target audio signal and a reference audio signal provided by a client, wherein the target audio signal and the reference audio signal are originated from different audio acquisition terminals, and the audio acquisition terminals are located in different positions of a same location; determining a filter coefficient corresponding to the target audio signal based on the reference audio signal; and eliminating, from the target audio signal, a crosstalk signal determined based on the filter coefficient and the reference audio signal.

Another embodiment provides an electronic device, comprising a network communication unit and a processor, wherein the network communication unit is configured to receive a target audio signal and a reference audio signal provided by a client, wherein the target audio signal and the reference audio signal are originated from different audio acquisition terminals, and the audio acquisition terminals are located in different positions of a same location; and the processor is configured to determine a filter coefficient corresponding to the target audio signal based on the reference audio signal; and eliminate, from the target audio signal, a crosstalk signal determined based on the filter coefficient and the reference audio signal.

Another embodiment provides a method for processing audio signals, comprising: receiving a first audio signal inputted from a first audio acquisition terminal and a second audio signal inputted from a second audio acquisition terminal, wherein the first audio acquisition terminal and the second audio acquisition terminal are located in different positions of a same location; and sending the first audio signal and the second audio signal to a server, so that the server determines a target audio signal and a reference audio signal from the first audio signal and the second audio signal; determines a filter coefficient corresponding to the target audio signal based on the reference audio signal; and eliminates, from the target audio signal, a crosstalk signal determined based on the filter coefficient and the reference audio signal.

Another embodiment provides a client, comprising: a first audio acquisition terminal, configured to input a first audio signal; a second audio acquisition terminal, configured to input a second audio signal, wherein the first audio acquisition terminal and the second audio acquisition terminal are located in different positions of a same location; and a network communication unit, configured to send the first audio signal and the second audio signal to a server, so that the server determines a target audio signal and a reference audio signal from the first audio signal and the second audio signal; determines a filter coefficient corresponding to the target audio signal based on the reference audio signal; and eliminates, from the target audio signal, a crosstalk signal determined based on the filter coefficient and the reference audio signal.

Another embodiment provides a method for processing audio signals, comprising: receiving a first audio signal and a second audio signal provided by a client, wherein the first audio signal and the second audio signal are originated from different audio acquisition terminals, and the audio acquisition terminals are located in different positions of a same location; determining a target audio signal and a reference audio signal from the first audio signal and the second audio signal; determining a filter coefficient corresponding to the target audio signal based on the reference audio signal; and eliminating, from the target audio signal, a crosstalk signal determined based on the filter coefficient and the reference audio signal.

Another embodiment provides an electronic device, comprising a network communication unit and a processor, wherein the network communication unit is configured to receive a first audio signal and a second audio signal provided by a client, wherein the first audio signal and the second audio signal are originated from different audio acquisition terminals, and the audio acquisition terminals are located in different positions of a same location; and the processor is configured to determine a target audio signal and a reference audio signal from the first audio signal and the second audio signal; determine a filter coefficient corresponding to the target audio signal based on the reference audio signal; and eliminate, from the target audio signal, a crosstalk signal determined based on the filter coefficient and the reference audio signal.

According to the above technical solutions provided in the disclosed embodiments, a target audio signal and a reference audio signal are determined, and the target audio signal is processed according to the reference speech to decrease an audio signal, in the target audio signal, tending to be originated from the same sound source as the reference audio signal. In this way, crosstalk generated by the sound source of the reference audio signal in the target audio signal can be eliminated to the greatest extent. Thus, a speech path can output speech signals with less interference.

BRIEF DESCRIPTION OF THE DRAWINGS

The drawings used in the description of the embodiments are introduced briefly herein. The drawings described below are merely some of the disclosed embodiments, and those of ordinary skill in the art may still derive other drawings from these drawings without significant efforts.

DETAILED DESCRIPTION OF THE EMBODIMENTS

To enable those skilled in the art to better understand the technical solutions, the technical solutions in the embodiments will be described clearly and completely below with reference to the drawings. The described embodiments are merely some, rather than all of the embodiments. On the basis of the disclosed embodiments, all other embodiments obtained by those of ordinary skill in the art without making creative efforts shall fall within the scope of the disclosure.

Figure 1:
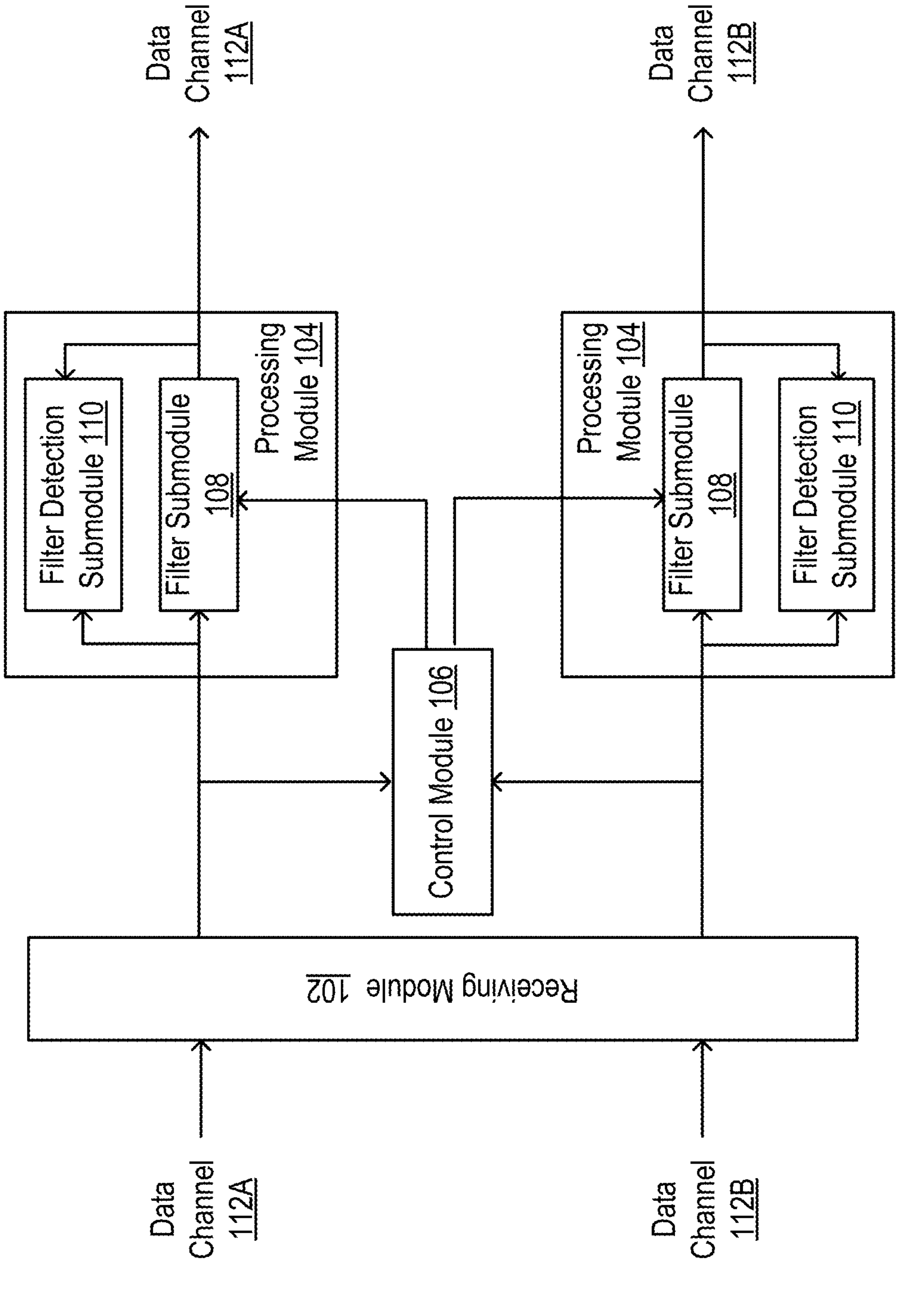
FIG. 1 is a block diagram of an audio data processing system according to some embodiments of the disclosure.
Figure 2:
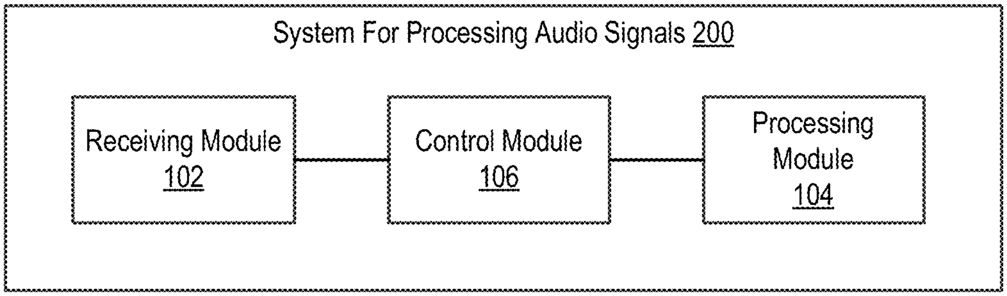
FIG. 2 is a block diagram of an audio data processing system according to some embodiments of the disclosure.
Figure 3:
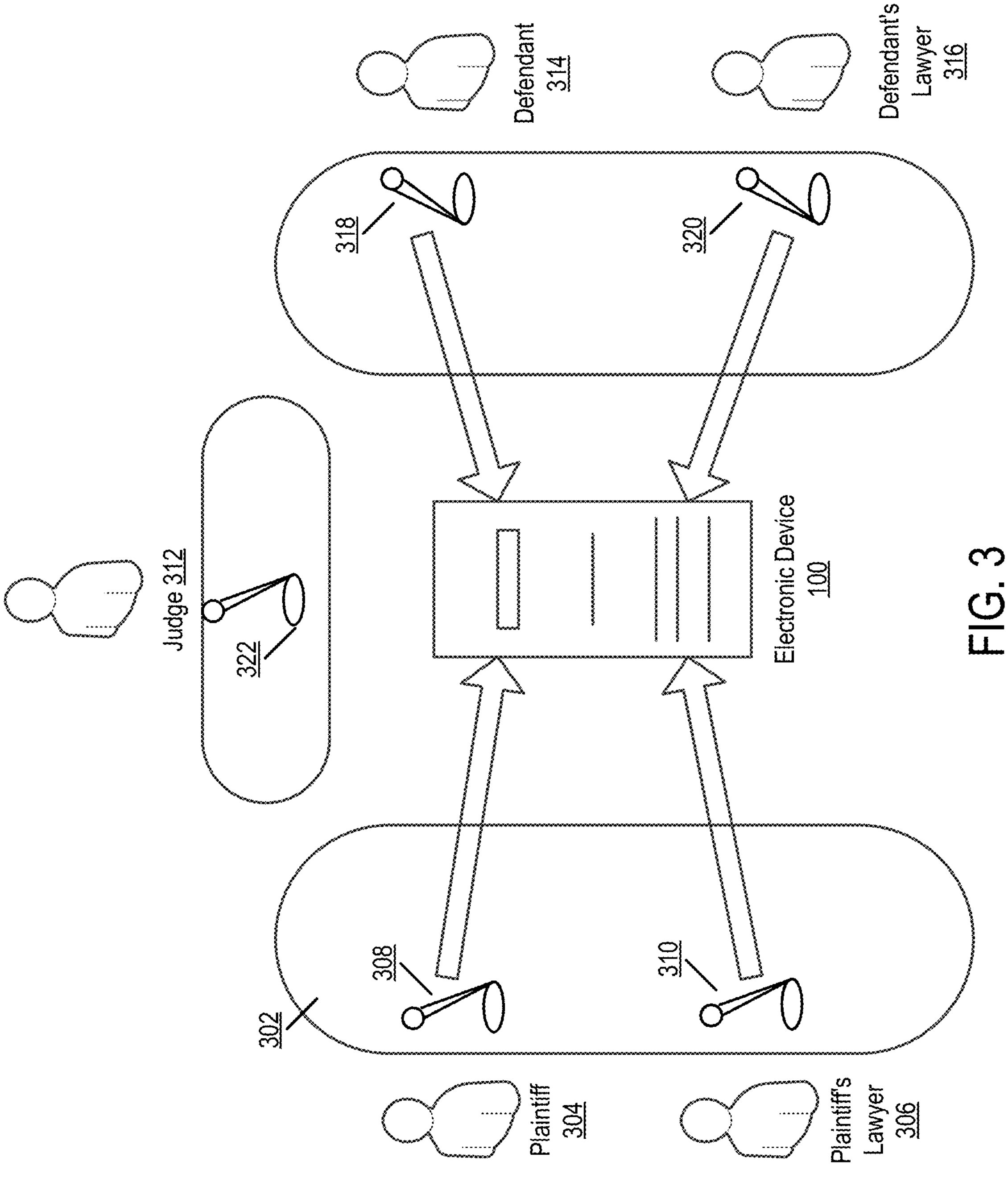
FIG. 3 is a block diagram of an audio data processing system provided in an embodiment of a court trial scenario.

Referring to FIGS. 1 through 3, a scenario example is shown. In plaintiff's seats (302) at the scene of a court trial, a plaintiff (304) and a plaintiff's lawyer (306) each have microphones (308, 310) in front of them, and speech of the plaintiff (304) and the plaintiff's lawyer (306) are output through a power amplifier (not illustrated). Since the microphones (308, 310) in front of the plaintiff (304) and the plaintiff's lawyer (306) are close to each other, when either of the plaintiff (304) or the plaintiff's lawyer (306) speaks, both of the microphones (308, 310) in front of them can sense sound to generate audio signals. For example, when the plaintiff (304) is speaking, the microphone (308) in front of the plaintiff can sense the speech of the plaintiff (304), and the microphone (310) in front of the plaintiff's lawyer (306) can also sense the speech of the plaintiff (304). In this case, the microphone (310) in front of the plaintiff's lawyer (306) may sense the speech of the plaintiff (304) to generate an audio signal, which forms crosstalk and produces interference.

In this example, an electronic device (100) may be provided. The electronic device (100) may include a receiving module (102) and a processing module (104) as illustrated in FIGS. 1 and 2.

In one embodiment, while the plaintiff (304) is speaking, the electronic device (100) receives audio signals provided by the microphones (308, 310, 318, 320, 322) through a receiving module (102). The receiving module (102) may have multiple data channels (112*a*, 112*b*) corresponding in number to the microphones (308, 310, 318, 320, 322). In one embodiment, the receiving module (102) receives the audio signals of the microphones by means of a Bluetooth® interface and protocol.

In one embodiment, a control module (106) may determine a reference audio signal and a target audio signal according to an audio signal inputted from the microphone (308) in front of the plaintiff (304) and an audio signal inputted from the microphone (310) in front of the plaintiff's lawyer (306) that are provided by the receiving module (102). Based on the principle that the energy of sound attenuates during propagation of the sound, the control module (106) determines the reference audio signal and the target audio signal according to the energy of the inputted audio signals.

In this example, the control module (106) calculates, according to the currently received audio signals inputted from the microphone (310) of the plaintiff's lawyer (306) and the microphone (308) of the plaintiff (304), smoothed energy of the audio signals. For example, the control module (106) may calculate that the smoothed energy of the audio signal inputted from the microphone (308) in front of the plaintiff (304) is 500 Joules, and the smoothed energy of the audio signal inputted from the microphone (310) in front of the plaintiff's lawyer (306) is 200 Joules. Since the smoothed energy of the audio signal inputted from the microphone (308) in front of the plaintiff (304) is greater than the smoothed energy of the audio signal inputted from the microphone (310) in front of the plaintiff's lawyer (308), the audio signal inputted from the microphone (308) in front of the plaintiff (304) may be used as the reference audio signal, and the audio signal inputted from the microphone (310) in front of the plaintiff's lawyer (308) includes an audio signal originated from the plaintiff (304) and may be used as the target audio signal to be processed. Further, the microphone (308) in front of the plaintiff (304) is in an active state, and the other microphones are considered to be in an inactive state.

In one embodiment, the control module (106), in the case that a difference between the smoothed energy of the reference audio signal and the smoothed energy of the target audio signal is greater than a set threshold, enables a processing module (104) corresponding to a data channel (112*a*, 112*b*) for transmitting the target audio signal and input the reference audio signal to the processing module (104). The control module (106) may set a threshold of 50 Joules. After the reference audio signal and the target audio signal are determined, the smoothed energy of the target audio signal is subtracted from the smoothed energy of the reference audio signal to obtain a difference of 300 Joules, which is greater than the set threshold.

In one embodiment, the processing module (104) may include a filter submodule (108) and a filter detection submodule (110). The filter submodule (108) is configured to output an audio signal obtained after the target audio signal is filtered. The filter detection submodule (110) is configured to detect whether the audio signal outputted after processing by the filter submodule (108) achieves a filtering effect.

In this example, the control module (106) enables the processing module (104) on a data channel (112*a*) for transmitting the audio signal of the plaintiff's lawyer (306). The filter submodule (108) may adaptively adjust a filter coefficient. The filter submodule (108) may use the audio signal inputted from the microphone (310) of the plaintiff's lawyer (306) as a reference and adjust the filter coefficient by using a gradient descent algorithm until a minimum difference is obtained between the audio signal outputted after the reference audio signal is filtered by the filter submodule (108) and the audio signal inputted from the microphone (310) of the plaintiff's lawyer (306). The filter submodule (108) may filter the target audio signal according to the finally obtained filter coefficient, so as to filter out a crosstalk audio signal in the target audio signal.

In one embodiment, the filter detection submodule (110) sets a threshold of 30 Joules, and the energy of the audio signal outputted from the filter submodule (108) is calculated as 100 Joules. The energy of the audio signal transmitted from the microphone (310) of the plaintiff's lawyer (306) is subtracted from the energy of the audio signal outputted from the filter submodule (108) to obtain a difference of −100 Joules, which is less than the set threshold. The filter detection submodule (110), in the case that the energy of the audio signal outputted from the filter submodule (108) minus the energy of the audio signal transmitted from the microphone (310) of the plaintiff's lawyer (306) is greater than the set threshold, resets the filter coefficient of the filter submodule (108) until the set condition is satisfied. In one embodiment, since the energy difference is less than the threshold, the filter coefficient does not need to be reset, and the audio signal outputted from the filter submodule (108) is directly outputted.

In this example, the filter coefficient can be altered according to the magnitudes of the audio signals transmitted from the microphones (308, 310) of the plaintiff (304) and the plaintiff's lawyer (306), so as to decrease the audio signal originated from the plaintiff (304) in the audio signal transmitted from the microphone (310) of the plaintiff's lawyer (306) without affecting the audio signal transmitted from the microphone (308) of the plaintiff (304).

In this example, a court record is generated according to speeches of parties (304, 306, 312, 314, 316) at the scene of the court trial, and audio signals transmitted from the microphone (308) of the plaintiff (304) and audio signals transmitted from the microphone (310) of the plaintiff's lawyer (306) may be sent to a server and respectively stored into different audio files. Since audio signals stored in each audio file all have reduced crosstalk interference, it is easy to generate a more accurate court record.

Figure 4:
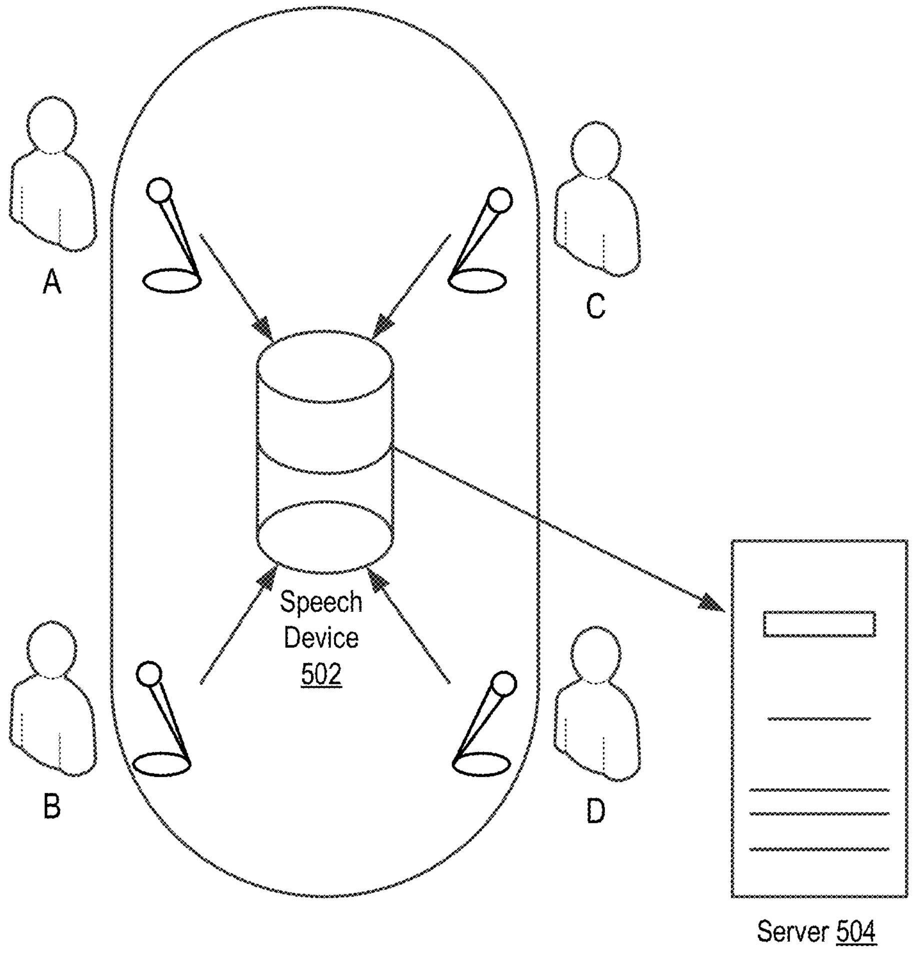
FIG. 4 is a block diagram of an audio data processing system according to some embodiments of the disclosure.
Figure 5:
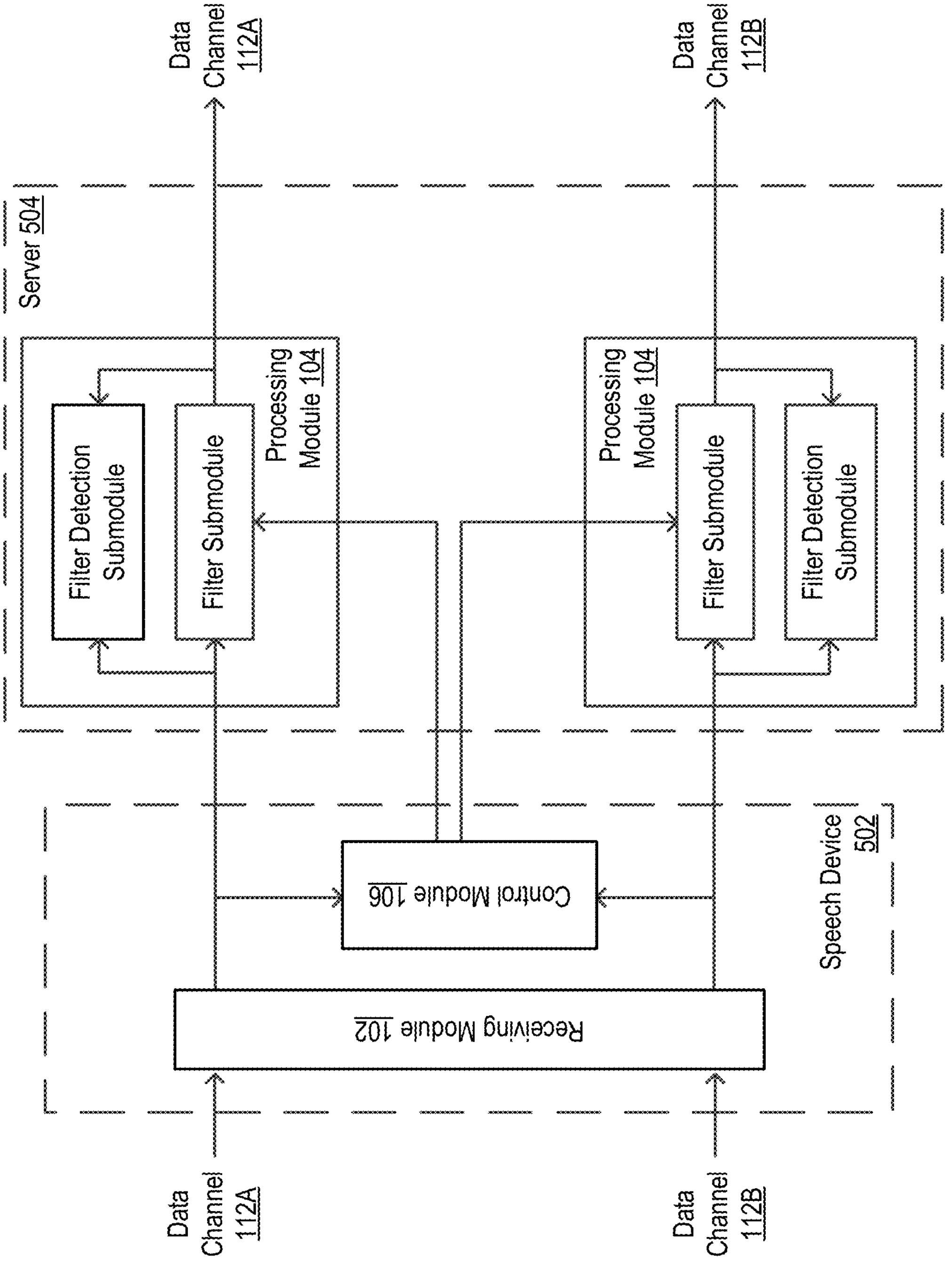
FIG. 5 is a block diagram of a meeting application scenario according to some embodiments of the disclosure.

Reference is made to FIG. 4 and FIG. 5. In a scenario example, at the scene of a meeting, participants A, B, C, and D each have a microphone in front of them, and speeches of participants A and B are outputted through a power amplifier (not illustrated). Since the microphones are close to each other, when a participant speaks, all microphones close to the speaker can sense sound to generate audio signals. In this case, in addition to a microphone right in front of the speaker, other microphones close to the speaker may sense the speech of the speaker to generate audio signals, which form crosstalk and produce ineffective interference.

In one embodiment, a speech device (502) is provided at the scene of the meeting and a server (504) is run using a cloud computing technology.

In one embodiment, the speech device (502) includes a receiving module (102), a control module (106), and (in some embodiments) a sending module (not illustrated).

In one embodiment, while participant A is speaking to the microphone, the speech device (502) receives audio signals provided by the microphones through the receiving module. The receiving module (102) may have multiple data channels (112*a*, 112*b*) corresponding in number to the microphones. The receiving module (102) receives, by means of Wi-Fi (Wireless Fidelity), the audio signals inputted by the microphones to the data channels (112*a*, 112*b*).

In one embodiment, the control module (106) may determine a reference audio signal and a target audio signal according to an audio signal inputted from the microphone right in front of participant A and audio signals inputted from other microphones that are provided by the receiving module (102). Based on the principle that the sound pressure of sound attenuates during the propagation of the sound, the control module (106) determines the reference audio signal and the target audio signal according to sound pressures of the inputted audio signals.

In one embodiment, the control module (106) calculates, according to audio signals inputted from the microphone right in front of A and the microphone of C, sound pressures of the audio signals. It is calculated that the energy of the audio signal inputted from the microphone right in front of A is 50 dBA, and the sound pressure of the audio signal inputted from the microphone of C is 25 dBA. Since the sound pressure of the audio signal inputted from the microphone right in front of A is greater than the sound pressure of the audio signal inputted from the microphone of C, the audio signal inputted from the microphone right in front of A may be used as the reference audio signal, and the audio signal inputted from the microphone of C includes an audio signal originated from A and may be used as the target audio signal to be processed.

In one embodiment, a sending module (not illustrated) sends the reference audio signal and the target audio signal determined by the control module (106) to the server (504) by means of Bluetooth or via a wide or local area network.

In one embodiment, the server (504) includes a filter submodule (108) and a filter detection submodule (110) included in a processing module (104) connected to each data channel (112*a*, 112*b*). The server (504) enables the filter submodule (108) upon receiving the reference audio signal and the target audio signal sent by the speech device (502).

In one embodiment, the filter submodule (108) may adjust a filter coefficient by using a minimum mean square error algorithm of a Wiener filter until a minimum difference is obtained between an audio signal outputted after the reference audio signal is filtered by the filter and the target audio signal. At this point, the target audio signal may be filtered according to the obtained filter coefficient. A crosstalk audio signal is filtered out from the target audio signal.

In one embodiment, a filter detection submodule (110) sets a threshold of 5 dBA, and a sound pressure value of the audio signal outputted from the filter submodule (108) is calculated as 31 dBA. The sound pressure value of the target audio signal is subtracted from the sound pressure value of the audio signal outputted from the filter submodule (108) to obtain a difference of 6 dBA, which is greater than the set threshold. The filter detection submodule (110) sets to, in the case that the sound pressure of the audio signal outputted from the filter submodule (108) minus the energy of the target audio signal is greater than the set threshold, reset the filter coefficient of the filter submodule (108) until the set condition is satisfied.

In one embodiment, since the sound pressure value is greater than the threshold, the filter coefficient needs to be reset, and the filter coefficient is adjusted again, so that the sound pressure value of the audio signal outputted from the filter submodule (108) is 29 dBA, which has a difference from the target audio signal less than the set threshold.

In one embodiment, the filter coefficient may be altered according to the magnitudes of the audio signals generated by the microphone right in front of A and the microphone of C, so as to decrease the audio signal originated from A in the audio signal generated by the microphone of C without affecting the audio signal generated by the microphone right in front of A.

In one embodiment, the server (504) may respectively store audio signals generated by the microphone right in front of A and audio signals generated by other microphones into different audio files. Since audio signals stored in each audio file all have reduced crosstalk interference, it is easy to generate a more accurate meeting record.

In one embodiment, the control module (106) sets a threshold of 40 dBA. When persons speak at the same time, someone has a louder voice and someone has a lower voice, and when a sound pressure value of an audio signal having a small sound pressure value is greater than 40 dBA, the audio signal having the small sound pressure value does not need to be processed. Audio signals of other persons having low voices are prevented from being mistakenly eliminated.

FIG. 2 is a block diagram of an audio data processing system according to some embodiments of the disclosure.

The audio data processing system (200) may include a receiving module (104), a control module (106), and a processing module (104). Accordingly, while running, the audio data processing system (200) can implement a method for processing audio data. Reference may be made to the corresponding explanation for the method for processing audio data, which will not be described again.

The receiving module (104) may receive a first audio signal inputted from a first audio acquisition terminal and a second audio signal inputted from a second audio acquisition terminal, where the first audio acquisition terminal and the second audio acquisition terminal are located in different positions of a same location. The first audio acquisition terminal may correspond to a first data channel, and the second audio acquisition terminal may correspond to a second data channel.

In one embodiment, the receiving module (104) may be a receiving device, or a communication module having data interaction capabilities. The receiving module (104) may receive, in a wired manner, the first audio signal inputted from the first data channel and the second audio signal inputted from the second data channel. The first audio signal inputted from the first data channel and the second audio signal inputted from the second data channel may also be received based on a network protocol such as HTTP, TCP/IP, or FTP or through a wireless communication module such as a Wi-Fi module, a ZigBee® module, a Bluetooth® module, or a Z-wave module. The audio acquisition terminal may be configured to record a user's sound to generate an audio signal. The audio signal is provided to the receiving module. Each audio acquisition terminal may be a transducer or a microphone provided with a transducer. The transducer is configured to convert a sound signal into an electrical signal to obtain an audio signal.

In one embodiment, the receiving module (104) may have multiple data channels corresponding in number to speech devices. The speech devices may include a device for sensing speech and generating an audio signal. The audio signal may include a data stream generated in the speech device from a speech emitted from a sound source. The audio signal may be a discrete data sequence or a continuous waveform. A speech emitted from the same sound source may be sensed by different speech devices to generate corresponding audio signals.

In one embodiment, the first audio acquisition terminal and the second audio acquisition terminal may be located at the same location. The same location may be a relatively spatially independent space. Specifically, for example, the same location may refer to a room, a square, or the like. The first audio acquisition terminal and the second audio acquisition terminal are located in different positions so that the audio acquisition terminals can respectively be positioned near, and/or positioned toward, corresponding users.

The control module (106) may determine a target audio signal and a reference audio signal from the first audio signal and the second audio signal. Accordingly, a data channel corresponding to the reference audio signal is in an active state. A processing module (104) corresponding to the data channel of the target audio signal may be enabled in the case that the target audio signal and the reference audio signal are determined. The manner of enabling the processing module (104) may include sending an instruction to the processing module (104) so that the control module (106) can receive an audio signal and perform processing. Those skilled in the art can also employ other alternative solutions, which should all be encompassed in the scope of the disclosure so long as the functions and effects achieved thereby are identical or similar to those.

In one embodiment, the data channels may include a carrier for transmitting an audio signal. The data channels may be a physical channel or a logical channel. The data channels may vary with a transmission path of the audio signal. The data channels may each correspond to a sound source. In the case that a data channel receives an audio signal originated from a corresponding sound source, the data channel is in an active state. Correspondingly, in the case that an audio signal received by a data channel is not originated from a corresponding sound source of the data channel, the data channel is in an inactive state. Specifically, for example, two microphones are provided, a sound source can emit a speech signal, and a channel of each microphone for transmitting the audio signal may be referred to as a data channel. Certainly, the data channel may also be logically divided, which may be understood as separately processing audio signals inputted from different microphones, that is, separately processing an audio signal inputted from one microphone instead of mixing audio signals inputted from multiple microphones.

In one embodiment, the target audio signal may be an audio signal including an audio signal tending to originate from the same sound source as the reference audio signal, and the energy of the target audio signal is less than that of the reference audio signal. It is needed to reduce an audio signal originated from the same sound source as the reference audio signal in the target audio signal, so that an audio signal finally outputted from each data channel can accurately correspond to a user using a microphone corresponding to the data channel. Specifically, for example, at the scene of a meeting, a first participant has a microphone in front of him/her, and a second participant also has a microphone in front of him/her. At this point, the first participant speaks, the microphone in front of the first participant should acquire the speech of the first participant and generate an audio signal, but since the microphone of the second participant is close to the microphone of the first participant, the microphone of the second participant may also acquire the speech of the first participant and generate an audio signal. In this case, the audio signal generated by the microphone of the second participant may be regarded as the target audio signal.

In one embodiment, the reference audio signal may include an audio signal emitted by a specified sound source and generated in a specified data channel. Specifically, for example, in a karaoke television (KTV) box, a person sings a song with a microphone in hand, and an audio signal generated in the microphone held in his/her hand from the sound produced by the singer may be used as the reference audio signal.

In one embodiment, the determining a target audio signal and a reference audio signal from the first audio signal and the second audio signal may include determining the target audio signal and the reference audio signal according to sound attribute values of the first audio signal and the second audio signal. The sound attribute values may include sound energy of sound, a sound pressure value of sound, frequency of sound, etc. Sound may attenuate during propagation depending on different transmission paths of the sound. Corresponding audio signals generated from speech signals received by the first data channel and the second data channel may also have different sound attribute values. The target audio signal and the reference audio signal may be determined according to at least one sound attribute value based on different sound output requirements. Specifically, for example, in the scenario of a meeting, a person is speaking, and multiple microphones can receive speech signals of the speech of the speaker and generate corresponding audio signals. Since the microphones are in different positions, transmission paths of sound waves are also different. To achieve a desirable speech output, an audio signal transmitted from a microphone closest to the speaker is generally selected as the reference audio signal. Audio signals transmitted from other microphones include audio signals generated from the speech of the speaker and are target audio signals. Since the energy of sound attenuates during propagation of the sound, the system may use the energy of an audio signal in each data channel as a reference for determining the target audio signal and the reference audio signal, use an audio signal having the greatest energy as the reference audio signal, and the others as the target audio signals.

In one embodiment, the control module (106) may enable the processing module (104) of the data channel of the target audio signal after the target audio signal and the reference audio signal are determined. The control module (106) may determine the target audio signal according to a comparison result of the first audio signal and the second audio signal, and then may determine which data channel the target audio signal is originated from. Each data channel may correspond to a processing module (104), and the control module (106) may send an enabling instruction to the processing module (104) of the data channel of the target audio signal, so as to enable the processing module (104) corresponding to the target data. In addition, a threshold may also be set, and the processing module (104) corresponding to the target audio signal is enabled in the case that a difference between the reference audio signal and the target audio signal is greater than the threshold.

The processing module (104) may determine a filter coefficient corresponding to the target audio signal based on the reference audio signal; and eliminate, from the target audio signal, a crosstalk signal determined based on the filter coefficient and the reference audio signal. The processing module (104) may filter the target audio signal according to the filter coefficient to decrease an audio signal, in the target audio signal, tending to be originated from the same sound source as the reference audio signal. The processing module (104) can correspond to the data channel.

In one embodiment, the audio signal, in the target audio signal, tending to be originated from the same sound source as the reference audio signal may be a crosstalk audio signal. An audio signal generated by a specified sound source in a specified data channel may be regarded as a reference audio signal, and an audio signal generated in any other data channel by the specified sound source or a sound source very close to and tending to be the same as the specified sound source, for example, in a scenario where two persons speak at the same time using the same microphone, may be regarded as a crosstalk audio signal.

In one embodiment, the processing module (104) may process the target audio signal according to the reference audio signal, which may include filtering out, from the target audio signal, the audio signal originated from the same sound source as the reference audio signal.

In one embodiment, the processing module (104) may include a filter submodule (illustrated in, for example, FIG. 1). The filter submodule may include a hardware device having a data filtering function and software required for driving the hardware device to operate. Certainly, the filter submodule may also be only a hardware device having filtering capabilities or only software running on a hardware device. The filter submodule may filter out a crosstalk signal in the target audio signal. An audio signal, in the target audio signal, tending to be originated from the same sound source as the reference audio signal can be reduced to the greatest extent. In the case that the control module (106) enables the processing module (104) provided on the channel for transmitting the target audio signal, the filter submodule may obtain a crosstalk audio signal corresponding to the target audio signal according to the reference audio signal, so as to further filter out the crosstalk audio signal from the target audio signal.

In one embodiment, the reference audio signal may be inputted to the filter submodule, and the filter submodule may determine a filter coefficient according to the reference audio signal, and use a product of the reference audio signal and the filter coefficient as a crosstalk audio signal of the target audio signal. The filter coefficient may be determined according to the reference audio signal. Specifically, the filter coefficient may be calculated iteratively according to a specified algorithm such as a gradient descent algorithm, a recursive least squares algorithm, or a minimum mean square error algorithm. In one embodiment, the filter coefficient may be constant, and in the case that the target audio signal is stable, the filter coefficient may not be altered. A product of the reference audio signal and the filter coefficient may be used as the crosstalk audio signal. In this way, the crosstalk audio signal is filtered out from the target audio signal to obtain the filtered target audio signal. Certainly, the filter coefficient may also be variable, and in the case that the target audio signal is unstable, the filter coefficient may be altered to obtain speech output of higher quality. The filter coefficient corresponding to the target audio signal outputted after filtering may be obtained by iteration through a specified algorithm for a filter such as an adaptive filter or a Wiener filter using the reference audio signal as a reference.

In one embodiment, the determining, by the control module (106), an audio signal and a reference audio signal from the first audio signal and the second audio signal may include: determining one of the first audio signal and the second audio signal having greater energy as the reference audio signal, and the other as the target audio signal; or determining one of the first audio signal and the second audio signal having a greater sound pressure value as the reference audio signal, and the other as the target audio signal; or determining one of the first audio signal and the second audio signal having a greater sound pressure value and greater energy as the reference audio signal, and the other as the target audio signal.

In one embodiment, an audio data block may be used as a unit for calculating the energy of each audio data block. For example, the first audio signal and the second audio signal are separately divided to obtain an audio data block, for example, the first audio signal is divided to obtain a first audio data block, and the second audio signal is divided to obtain a second audio data block. Certainly, the audio signal may also refer to an audio data block obtained by dividing an audio data stream, or refer to an entire audio data stream. Based on the principle that the energy of sound attenuates during propagation of the sound, an audio data block having greater energy in the first audio data block and the second audio data block is used as the reference audio signal, and an audio data block having less energy is used as the target audio signal. An audio data block is used as a unit for calculating the energy of each audio data block, so that the reference audio signal and the target audio signal can be determined in the scenario of alternate speaking. Specifically, in the scenario of speaking in turn, a person speaks to a microphone in front of him/her and then another person speaks to a microphone in front of himself/herself and beside the first person. In this case, the reference audio signal and the target audio signal change, and the energy of audio data blocks in the first audio signal and the second audio signal is calculated, so that the reference audio signal and the target audio signal can be accurately determined in the scenario of alternate speaking.

In one embodiment, for example, every 10 milliseconds of the audio signal may be used as one audio data block. Certainly, the audio data block may not be limited to 10 milliseconds. Or, the audio data block is obtained by division according to the amount of data. For example, each audio data block may be at most 5 MB. Or, an audio data block is obtained by division according to whether the sound waveform of the audio signal is continuous. For example, if duration of silence exists between two continuous neighboring waveforms, division is performed to use each continuous sound waveform as one audio data block. Energy corresponding to each audio data block may be calculated. Based on the principle that the energy of sound attenuates during propagation of the sound, an audio data block having greater energy is used as the reference audio signal, and an audio data block having less energy is used as the target audio signal.

In one embodiment, the determining one of the first audio signal and the second audio signal having a greater sound pressure value as the reference audio signal, and the other as the target audio signal may include: dividing the audio signals into audio data blocks according to a certain rule, calculating sound pressure values in corresponding audio data blocks of the first audio signal and the second audio signal, and using, based on the principle that the sound pressure value of sound attenuates during propagation of the sound, an audio data block having a greater sound pressure value as the reference audio signal, and an audio data block having a smaller sound pressure value as the target audio signal. The corresponding audio data blocks of the first audio signal and the second audio signal may have similar or same generation time.

In one embodiment, an audio data block may be used as a unit for calculating sound pressure values of audio data blocks of the first audio signal and the second audio signal. In this way, the reference audio signal can be determined in the scenario of alternate speaking.

In one embodiment, the determining one of the first audio signal and the second audio signal having a greater sound pressure value and greater energy as the reference audio signal, and the other as the target audio signal may include: determining, according to the calculated sound pressure values and energy of the first audio signal and the second audio signal, in the case that the sound pressure value and the energy of one audio signal are greater than the sound pressure value and the energy of the other audio signal, the audio signal having the greater sound pressure value and energy as the reference audio signal, and the audio signal having the less sound pressure value and energy as the target audio signal.

In one embodiment, based on the principle that the energy and sound pressure value of sound attenuate during propagation of the sound, the reference speech signal and the target speech signal can be accurately determined according to the energy and/or sound pressure values of the audio signals. In addition, the reference speech signal and the target speech signal can be accurately determined in the scenario of alternate speaking by calculating the energy and sound pressure values using an audio data block as a unit.

In one embodiment, the eliminating, by the processing module (104) from the target audio signal, a crosstalk signal determined based on the filter coefficient and the reference audio signal may include: processing the target audio signal only in the case that energy or a sound pressure value of the target audio signal is less than or equal to a specified threshold.

In one embodiment, the specified threshold may include a maximum of the energy or the sound pressure value of the target audio signal when the target audio signal obtained by those skilled in the art according to experience or estimation is an audio signal tending to be originated from the same sound source as the reference audio signal. In the case that the energy or the sound pressure value of the target audio signal is greater than the specified threshold, it may be considered that the target audio signal is not an audio signal originated from the same sound source as the reference audio signal. In the case that the energy or sound pressure value of the target audio signal is less than or equal to the specified threshold, it may be considered that the target audio signal includes an audio signal tending to be originated from the same sound source as the reference audio signal; in this case, the target audio signal may be processed to decrease the audio signal, in the target audio signal, tending to be originated from the same sound source as the reference audio signal. Specifically, for example, when two persons speak to respective microphones at the same time, the microphones of the two persons have input of speech of different persons at the same time, and audio signals in the two microphones both have great energy or sound pressure values, and it cannot be considered, just because the energy or sound pressure value of an audio signal in one microphone is less than the energy or sound pressure value of an audio signal in the other microphone, that the audio signal having the less energy or sound pressure value is an audio signal originated from the same sound source as the audio signal having the greater energy or sound pressure value so as to perform processing.

In one embodiment, a specified threshold is set, and the target audio signal is processed only in the case that the energy or the sound pressure value of the target audio signal is less than or equal to the specified threshold, so as to prevent an effective audio signal from being deceased and ensure output of the effective speech signal.

In one embodiment, the filter submodule (108) may calculate the filter coefficient according to a gradient descent algorithm. Specifically, reference may be made to the following equation (1):

$$W(n)=w(n-1)+\mu[\gamma+x(n)*x(n)T]^{-1}*x(n)*(d(n)-x(n)^{T}w(n-1)) \qquad \text{Equation (1)}$$

In the above equation (1), n may be used for representing a sequence number of an audio data segment of an audio data block, w(n) may be a filter coefficient of the $n^{th}$ audio data segment, μ is an empirical value, γ is a normalized factor, x(n) may represent a reference audio signal, and d(n) may represent a target audio signal.

In one embodiment, the filter coefficient may be obtained according to the equation (1) so as to use a product of the filter coefficient and the reference audio signal as a crosstalk audio signal.

In one embodiment, the processing module (104) further includes a filter detection submodule (illustrated, for example, in FIG. 1) that may include a hardware device having a data processing function and software required for driving the hardware device to operate. Certainly, the filter detection submodule may also be only a hardware device having data processing capabilities or only software running on a hardware device. The filter detection submodule is configured to reset the filter submodule corresponding to the target audio signal in the case that the audio signal outputted from the filter submodule satisfies a set condition.

In one embodiment, a first data channel corresponding to the first audio acquisition terminal and a second data channel corresponding to the second audio acquisition terminal are respectively provided with filter submodules; and the step of eliminating, from the target audio signal, a crosstalk signal determined based on the filter coefficient and the reference audio signal includes: filtering out, by a filter submodule corresponding to the target audio signal, the crosstalk signal in the target audio signal.

In one embodiment, the set condition may include a preset condition that can indicate an undesirable filtering effect of the filter submodule if the set condition is satisfied. Specifically, for example, the set condition may include that energy or a sound pressure value of the audio signal outputted from the filter submodule or other parameters characterizing sound attributes of the audio signal have no change or a small change; data obtained after filtering of the target audio signal has a great change or obviously does not conform to a due filtering result, or the like.

In one embodiment, a condition is set, and the filter submodule corresponding to the target audio signal is reset in the case that the processed target audio signal satisfies the set condition, so as to realize system self-test for filtering, ensure output of a target audio signal satisfying conditions from the filter submodule, and improve system stability.

In one embodiment, the set condition may include: energy of the processed target audio signal is greater than energy of the target audio signal before processing; or a sound pressure value of the processed target speech is greater than a sound pressure value of the target audio signal before processing.

In one embodiment, in the case that the energy of the processed target audio signal is greater than the energy of the target audio signal before processing, or the sound pressure value of the processed target speech is greater than the sound pressure value of the target audio signal before processing, it can be determined that the target audio signal has a gain after being processed by the filter submodule, and thus it can be determined that the audio signal, in the target audio signal, originated from the same sound source as the reference audio signal after being processed by the filter submodule is not filtered out, and this may in turn affect speech output of the system. It is thus needed to reset the filter coefficient.

In one embodiment, to further improve system stability, a threshold may be given, and the filter coefficient is reset in the case that a difference between the sound pressure values or energy before and after processing of the filter submodule is greater than the given threshold.

In one embodiment, the processing module (104) processes the target audio signal according to the reference audio signal to decrease the audio signal, in the target audio signal, tending to be originated from the same sound source as the reference audio signal, thereby effectively preventing a useful audio signal in the target audio signal from being mistakenly eliminated during signal processing.

In one embodiment, an audio signal inputted from the first data channel and an audio signal inputted from the second data channel may be stored into different audio files.

In one embodiment, the audio signal inputted from the first data channel may be stored into one audio file, and the audio signal transmitted from the second data channel may be stored into another audio file. Each audio file may correspond to an audio signal having subjected to crosstalk processing. Each audio file may correspond to one channel, and may therefore correspond to each sound source. Thus, an audio signal with reduced crosstalk transmitted in each channel can be conveniently obtained, facilitating subsequent use of the audio signal.

Figure 6:
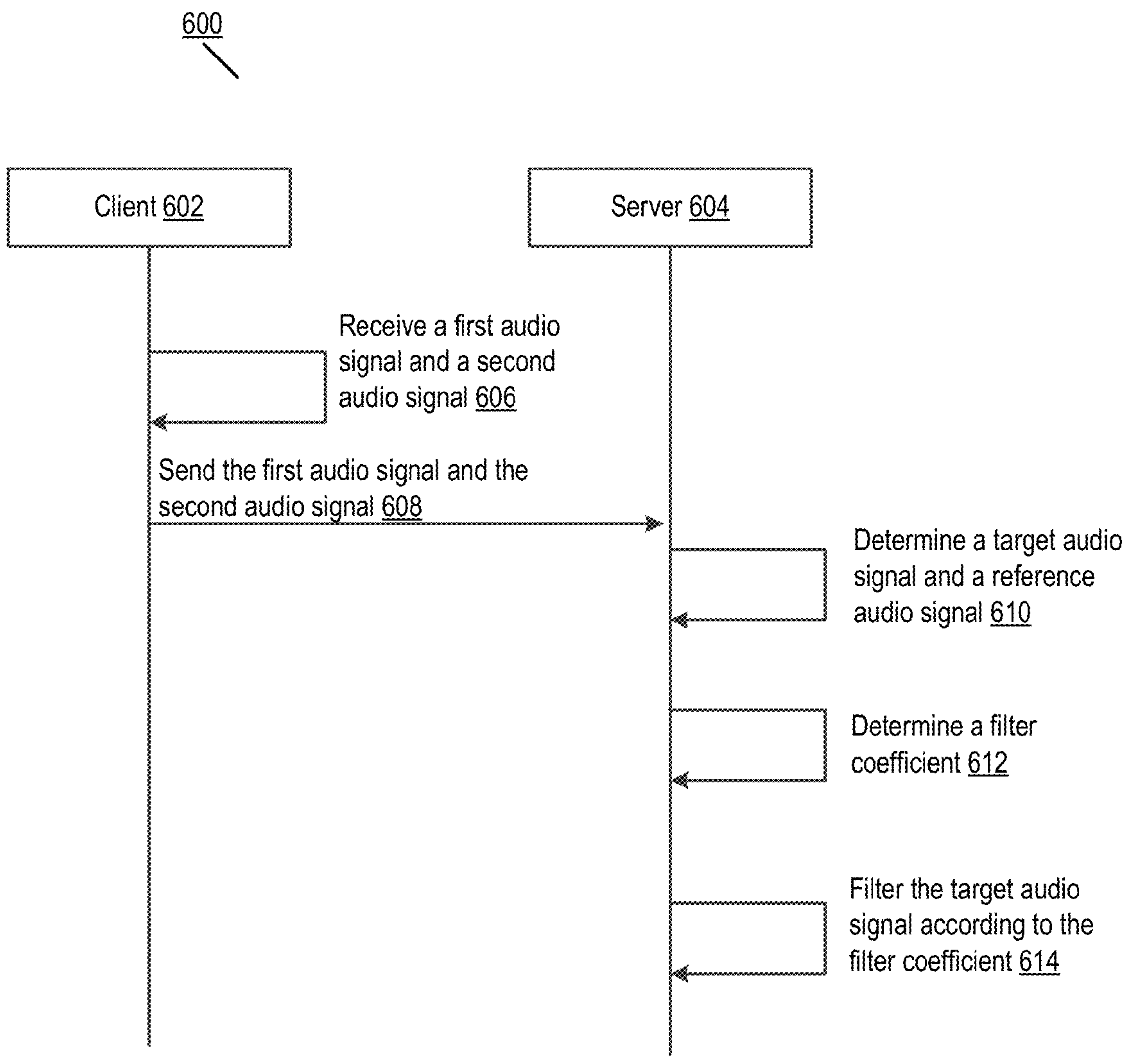
FIG. 6 is a flow diagram of an audio data processing system according to some embodiments of the disclosure.

FIG. 6 is a flow diagram of an audio data processing system (600) according to some embodiments of the disclosure. The information processing system (6000 may include a client (602) and a server (604).

In one embodiment, the client (602) may include at least two audio acquisition terminals and a network communication unit.

In one embodiment, the client (602) may have the receiving module (described previously). The audio acquisition terminal may be configured to record a user's speech to generate an audio signal. The audio signal is provided to the receiving module. Each audio acquisition terminal may be a transducer or a microphone provided with a transducer. The transducer is configured to convert a sound signal into an electrical signal to obtain an audio signal. The network communication unit may perform network data communication in compliance with a network communication protocol. Specifically, for example, the client (602) may be an electronic device having poor data processing capabilities, such as an Internet of Things (IoT) device.

In one embodiment, the client (602) may generate audio signals through at least two audio acquisition terminals. Each audio acquisition terminal may correspond to one data channel. The client may send, through the network communication unit, the audio signals received by the receiving module to the server (604). Specifically, the at least two audio acquisition terminals may include a first audio acquisition terminal and a second audio acquisition terminal. Accordingly, the first audio acquisition terminal may correspond to a first data channel, and the second audio acquisition terminal may correspond to a second data channel.

In one embodiment, the server (604) may be an electronic device having certain computing and processing capabilities. The server (604) may have a network communication unit, a processor, a memory, and the like. Certainly, the aforementioned server (604) may also refer to software running on the electronic device. The aforementioned server (604) may also be a distributed server, which may be a system having multiple processors, memories, and network communication modules that operate collaboratively. Or, the server (604) may also be a server cluster formed by several servers. Certainly, the server (604) may also employ a cloud technology to implement the function of the server (604) by cloud computing.

The server (604) may run the control module (described previously) and the processing module (described previously) to process the target audio signal according to the reference audio signal, so as to decrease an audio signal, in the target audio signal, tending to be originated from the same sound source as the reference audio signal. The server (604) may be provided with a network communication module to receive or send data. The network communication module may serve as a receiving module of the server (604).

In one embodiment, the processor may be implemented in any appropriate manner. For example, the processor may employ the form of a microprocessor or processor and a computer-readable medium that stores computer-readable program code (for example, software or firmware) executable by the microprocessor, logic gates, switches, an application specific integrated circuit (ASIC), a programmable logic controller, and an embedded microcontroller.

Figure 7:
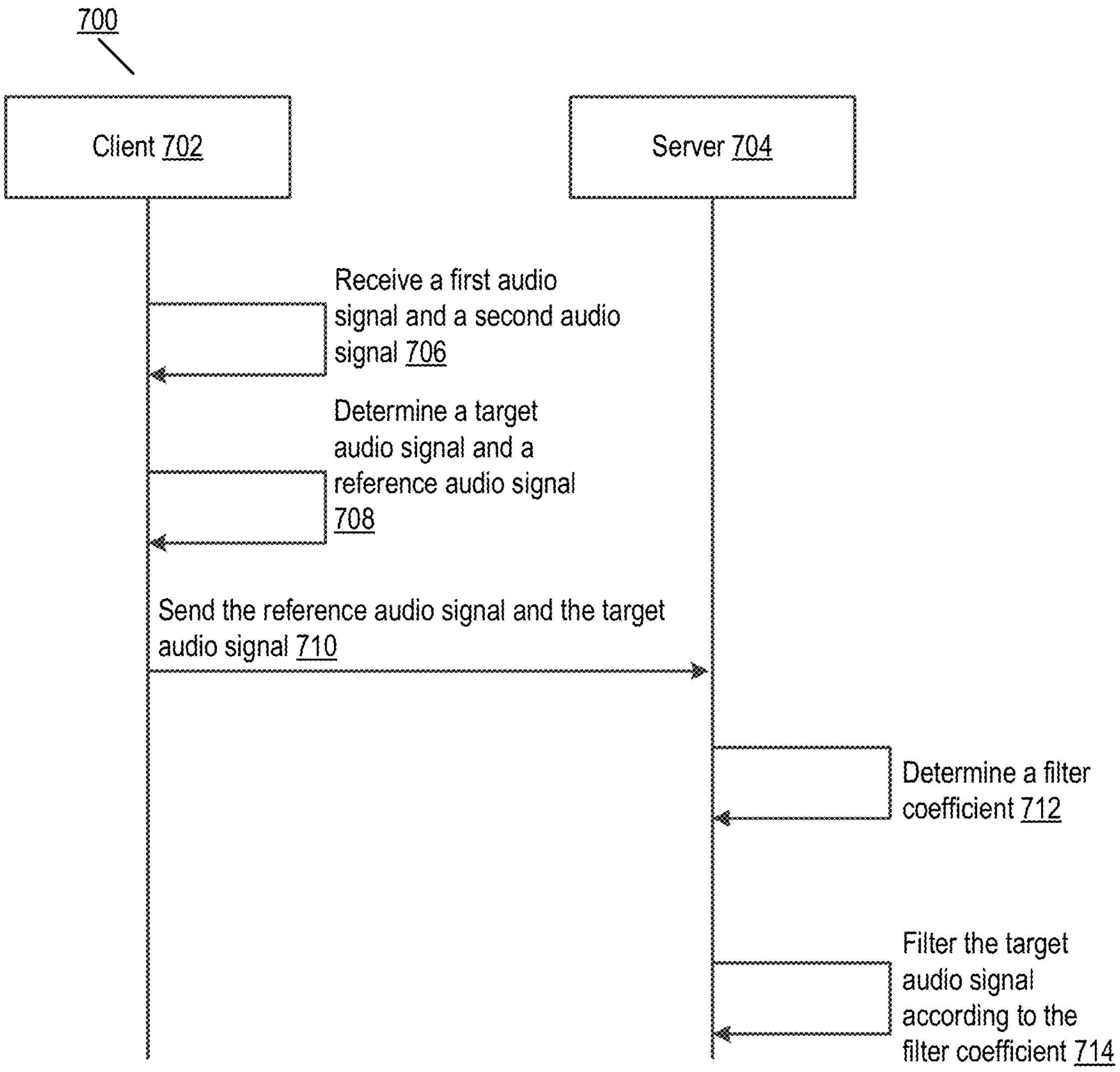
FIG. 7 is a flow diagram of an audio data processing system according to some embodiments of the disclosure.

FIG. 7 is a flow diagram of an audio data processing system according to some embodiments of the disclosure.

The client (702) thus has certain data processing capabilities. The client (702) at least can run the receiving module and the control module (106). Further, a target audio signal and a reference audio signal that are determined are provided to the server (704) through the network communication unit. Specifically, for example, the client (702) may be a laptop computer, a desktop computer, or a smart terminal device. In one embodiment, the server (704) may have the processing module (104) running thereon.

In another embodiment, the client (702) may include at least two audio acquisition terminals and a processor. The client (702) may have stronger data processing capabilities. In this way, the receiving module, the control module (106), and the processing module (104) all run on the client (702). In this scenario, it may not be needed to interact with the server (704). Or, an audio signal processed by the processing module (104) may be provided to the server (704). Specifically, for example, the client (702) may be a tablet computer, a laptop computer, a desktop computer, a workstation, or the like having high performance.

Certainly, some clients are listed above by way of example only. The performance of hardware device may be improved with the progress of science and technology, so that an electronic device currently having poor data processing capabilities will possibly have excellent data processing capabilities. As a result, the division of software modules running on the hardware device in the aforementioned embodiments does not constitute a limitation to the disclosure. Those skilled in the art may also perform further functional splitting on the aforementioned software modules and correspondingly deploy them in the client (702) or server (704) for running. The functional splitting should be encompassed in the scope of the disclosure so long as the functions and effects achieved thereby are identical or similar to those.

An embodiment provides a computer storage medium. The computer storage medium stores a computer program that, when executed by a processor, implements: receiving a first audio signal inputted from a first audio acquisition terminal and a second audio signal inputted from a second audio acquisition terminal (606), where the first audio acquisition terminal and the second audio acquisition terminal are located in different positions of a same location; sending the first audio signal and the second audio signal to a server (608); determining a target audio signal and a reference audio signal from the first audio signal and the second audio signal (610); determining a filter coefficient corresponding to the target audio signal based on the reference audio signal (612); and eliminating, from the target audio signal, a crosstalk signal determined based on the filter coefficient and the reference audio signal (614).

In one embodiment, the computer storage medium includes, but is not limited to, a random access memory (RAM), a read-only memory (ROM), a cache, a hard disk drive (HDD), or a memory card.

In one embodiment, the specific function implemented by the computer storage medium may be explained in contrast to the method for unlocking an electronic device in the present disclosure, and reference may be made to the corresponding explanation in other embodiments.

An embodiment provides a computer storage medium. The computer storage medium stores a computer program that, when executed by a processor, implements: receiving a first audio signal inputted from a first audio acquisition terminal and a second audio signal inputted from a second audio acquisition terminal, where the first audio acquisition terminal and the second audio acquisition terminal are located in different positions of a same location (706); determining a target audio signal and a reference audio signal from the first audio signal and the second audio signal (708); sending the target audio signal and the reference audio signal to a server (710), so that the server determines a filter coefficient corresponding to the target audio signal based on the reference audio signal (712); and eliminating, from the target audio signal, a crosstalk signal determined based on the filter coefficient and the reference audio signal (714).

In one embodiment, the computer storage medium includes, but is not limited to, a random access memory (RAM), a read-only memory (ROM), a cache, a hard disk drive (HDD), or a memory card.

In one embodiment, the specific function implemented by the computer storage medium may be explained in contrast to the method for unlocking an electronic device in the present disclosure, and reference may be made to the corresponding explanation in other embodiments.

An embodiment provides a computer storage medium. The computer storage medium stores a computer program that, when executed by a processor, implements: receiving a target audio signal and a reference audio signal provided by a client, where the target audio signal and the reference audio signal are originated from different audio acquisition terminals, and the audio acquisition terminals are located in different positions of a same location (710); determining a filter coefficient corresponding to the target audio signal based on the reference audio signal (712); and eliminating, from the target audio signal, a crosstalk signal determined based on the filter coefficient and the reference audio signal (714).

In one embodiment, the computer storage medium includes, but is not limited to, a random access memory (RAM), a read-only memory (ROM), a cache, a hard disk drive (HDD), or a memory card.

In one embodiment, the specific function implemented by the computer storage medium may be explained in contrast to the method for unlocking an electronic device in the present disclosure, and reference may be made to the corresponding explanation in other embodiments.

An embodiment provides a computer storage medium. The computer storage medium stores a computer program that, when executed by a processor, implements: receiving a first audio signal inputted from a first audio acquisition terminal and a second audio signal inputted from a second audio acquisition terminal, where the first audio acquisition terminal and the second audio acquisition terminal are located in different positions of a same location (606); and sending the first audio signal and the second audio signal to a server (608), so that the server determines a target audio signal and a reference audio signal from the first audio signal and the second audio signal (610); determines a filter coefficient corresponding to the target audio signal based on the reference audio signal (612); and eliminates, from the target audio signal, a crosstalk signal determined based on the filter coefficient and the reference audio signal (614).

In one embodiment, the computer storage medium includes, but is not limited to, a random access memory (RAM), a read-only memory (ROM), a cache, a hard disk drive (HDD), or a memory card.

In one embodiment, the specific function implemented by the computer storage medium may be explained in contrast to the method for unlocking an electronic device in the present disclosure, and reference may be made to the corresponding explanation in other embodiments.

An embodiment provides a computer storage medium. The computer storage medium stores a computer program that, when executed by a processor, implements: receiving a first audio signal and a second audio signal provided by a client (608), where the first audio signal and the second audio signal are originated from different audio acquisition terminals, and the audio acquisition terminals are located in different positions of a same location; determining a target audio signal and a reference audio signal from the first audio signal and the second audio signal (610); determining a filter coefficient corresponding to the target audio signal based on the reference audio signal (612); and eliminating, from the target audio signal, a crosstalk signal determined based on the filter coefficient and the reference audio signal (614).

In one embodiment, the computer storage medium includes, but is not limited to, a random access memory (RAM), a read-only memory (ROM), a cache, a hard disk drive (HDD), or a memory card.

In one embodiment, the specific function implemented by the computer storage medium may be explained in contrast to the method for unlocking an electronic device in the present disclosure, and reference may be made to the corresponding explanation in other embodiments.

The above description of various embodiments is provided for purposes of description to those skilled in the art. It is not intended to be exhaustive or to limit the disclosed embodiments to a single disclosed embodiment. As mentioned above, various alternatives and variations to the present disclosure will be apparent to those skilled in the art of the above technologies. Accordingly, although some embodiments have been discussed specifically, other embodiments will be apparent or relatively easily derived by those skilled in the art. The present disclosure is intended to embrace all the alternatives, modifications, and variations of the disclosed embodiments that have been discussed herein, and other embodiments that fall within the spirit and scope of the above described application.

The expressions "first" and "second" in the embodiments of the specification are only intended to distinguish between different data channels and do not define the number of data channels herein. The data channels may include multiple data channels and are not limited to only two data channels.

Through the above description of the embodiments, those skilled in the art can clearly understand that the disclosure can be implemented by means of software plus a necessary universal hardware platform. Based on such understanding, the technical solution of the disclosure in essence or the part that contributes to the prior art may be embodied in the form of a software product. The computer software product may be stored in a storage medium such as a ROM/RAM, a magnetic disk, or an optical disc, and include several instructions to instruct a computer device (which may be a personal computer, a server, a network device, or the like) to perform the methods described in the embodiments of the disclosure or in some parts of the embodiments.

The disclosed embodiments are described in a progressive manner, and for identical or similar parts between different embodiments, reference may be made to each other so that each of the embodiments focuses on differences from other embodiments.

The present disclosure may be used in various universal or specialized computer system environments or configurations. Examples include: a personal computer, a server computer, a handheld device or a portable device, a tablet device, a microprocessor-based system, a set-top box, a programmable consumer electronic device, a network PC, a small-scale computer, and a distributed computing environment including any system or device above.

Although the present disclosure is described through the embodiments, those of ordinary skill in the art know that the present disclosure has many modifications and variations without departing from the spirit. It is intended that the appended claims include these modifications and variations without departing from the spirit.

What is claimed is:

1. A method comprising:
receiving a first audio signal and a second audio signal;
identifying a target audio signal and a reference audio signal from the first and second audio signals by comparing sound attribute values of the first and second audio signals; and
processing the target audio signal, the processing comprising:
determining a filter coefficient corresponding to the target audio signal based on the reference audio signal,
eliminating, from the target audio signal, a crosstalk signal based on the filter coefficient and the reference audio signal to obtain a filtered target audio signal,
computing a filtered sound attribute value of the filtered target audio signal,
computing a difference between the filter sound attribute value and a sound attribute value associated with the target audio signal, and
resetting the filter coefficient when the difference exceeds a threshold value.

2. The method of claim 1, the receiving the first audio signal and the second audio signal comprising receiving the first audio signal and the second audio signal via first and second acquisition terminals situated in a same location.

3. The method of claim 1, the comparing sound attribute values of the first and second audio signals comprising comparing energy, sound pressure, or frequency values of the first and second audio signals.

4. The method of claim 1, the determining a filter coefficient comprising determining the filter coefficient using an algorithm selected from the group consisting of a gradient descent algorithm, a recursive least squares algorithm, or a minimum mean square error algorithm.

5. The method of claim 1, the determining a filter coefficient comprising iteratively setting the filter coefficient.

6. The method of claim 5, the iteratively setting the filter coefficient comprising setting the filter coefficient using an adaptive filter or Wiener filter.

7. The method of claim 1, further comprising segmenting the first audio signal and the second audio signal into a plurality of audio blocks and using the plurality of audio blocks as the first audio signal and the second audio signal.

8. A device comprising:
a processor; and
a storage medium for tangibly storing thereon program logic for execution by the processor, the stored program logic comprising:
logic, executed by the processor, for receiving a first audio signal and a second audio signal,
logic, executed by the processor, for identifying a target audio signal and a reference audio signal from the first and second audio signals by comparing sound attribute values of the first and second audio signals, and
logic, executed by the processor, for processing the target audio signal, the processing comprising:
determining a filter coefficient corresponding to the target audio signal based on the reference audio signal,
eliminating, from the target audio signal, a crosstalk signal based on the filter coefficient and the reference audio signal to obtain a filtered target audio signal,
computing a filtered sound attribute value of the filtered target audio signal;
computing a difference between the filter sound attribute value and a sound attribute value associated with the target audio signal; and
resetting the filter coefficient when the difference exceeds a threshold value.

9. The device of claim 8, the logic for receiving the first audio signal and the second audio signal comprising logic, executed by the processor, for receiving the first audio signal and the second audio signal via first and second acquisition terminals situated in a same location.

10. The device of claim 8, the logic for comparing sound attribute values of the first and second audio signals comprising logic, executed by the processor, for comparing energy, sound pressure, or frequency values of the first and second audio signals.

11. The device of claim 8, the logic for determining a filter coefficient comprising logic, executed by the processor, for determining the filter coefficient using an algorithm selected from the group consisting of a gradient descent algorithm, a recursive least squares algorithm, or a minimum mean square error algorithm.

12. The device of claim 8, the logic for determining a filter coefficient comprising logic, executed by the processor, for iteratively setting the filter coefficient.

13. The device of claim 12, the logic for iteratively setting the filter coefficient comprising logic, executed by the processor, for setting the filter coefficient using an adaptive filter or Wiener filter.

14. The device of claim 8, the stored program logic further comprising logic, executed by the processor, for segmenting the first audio signal and the second audio signal into a plurality of audio blocks and using the plurality of audio blocks as the first audio signal and the second audio signal.

15. A non-transitory computer readable storage medium for tangibly storing computer program instructions capable of being executed by a computer processor, the computer program instructions defining the steps of:
receiving a first audio signal and a second audio signal;
identifying a target audio signal and a reference audio signal from the first and second audio signals by comparing sound attribute values of the first and second audio signals; and
processing the target audio signal, the processing comprising:
determining a filter coefficient corresponding to the target audio signal based on the reference audio signal,
eliminating, from the target audio signal, a crosstalk signal based on the filter coefficient and the reference audio signal to obtain a filtered target audio signal,
computing a filtered sound attribute value of the filtered target audio signal,
computing a difference between the filter sound attribute value and a sound attribute value associated with the target audio signal, and resetting the filter coefficient when the difference exceeds a threshold value.

16. The non-transitory computer readable storage medium of claim 15, the receiving the first audio signal and the second audio signal comprising receiving the first audio signal and the second audio signal via first and second acquisition terminals situated in a same location.

17. The non-transitory computer readable storage medium of claim 15, the comparing sound attribute values of the first and second audio signals comprising comparing energy, sound pressure, or frequency values of the first and second audio signals.

18. The non-transitory computer readable storage medium of claim 15, the determining a filter coefficient comprising determining the filter coefficient using an algorithm selected from the group consisting of a gradient descent algorithm, a recursive least squares algorithm, or a minimum mean square error algorithm.

19. The non-transitory computer readable storage medium of claim 15, the determining a filter coefficient comprising iteratively setting the filter coefficient.

20. The non-transitory computer readable storage medium of claim 15, the computer program instructions further defining the step of segmenting the first audio signal and the second audio signal into a plurality of audio blocks and using the plurality of audio blocks as the first audio signal and the second audio signal.

* * * * *